United States Patent
Ujiie et al.

(10) Patent No.: US 8,268,300 B2
(45) Date of Patent: Sep. 18, 2012

(54) MATERIAL FOR ANEURYSM CURING

(75) Inventors: Hiroshi Ujiie, Tokyo (JP); Yoshiaki Suzuki, Tokyo (JP); Masaya Iwaki, Saitama (JP); Takanori Uchida, Kumamoto (JP)

(73) Assignees: RIKEN, Saitama (JP); The Chemo-Sero-Therapeutic Research Institute, Kumamoto (JP)

( * ) Notice: Subject to any disclaimer, the term of this patent is extended or adjusted under 35 U.S.C. 154(b) by 0 days.

(21) Appl. No.: 13/024,718

(22) Filed: Feb. 10, 2011

(65) Prior Publication Data

US 2011/0196415 A1 Aug. 11, 2011

Related U.S. Application Data

(62) Division of application No. 10/568,694, filed as application No. PCT/JP2004/012138 on Aug. 18, 2004, now abandoned.

(30) Foreign Application Priority Data

Aug. 19, 2003 (JP) .................................. 2003-207850

(51) Int. Cl.
*A61K 31/74* (2006.01)
(52) U.S. Cl. .................................................... 424/78.08
(58) Field of Classification Search .................. None
See application file for complete search history.

(56) References Cited

U.S. PATENT DOCUMENTS

| 5,152,783 A | 10/1992 | Suzuki et al. |
| 5,308,704 A * | 5/1994 | Suzuki et al. ................. 428/410 |
| 5,891,192 A | 4/1999 | Murayama et al. |
| 2002/0155295 A1 | 10/2002 | Suzuki et al. |
| 2007/0185570 A1 | 8/2007 | Ujiie et al. |

FOREIGN PATENT DOCUMENTS

| EP | 1252902 | 10/2002 |
| JP | 3-112560 | 5/1991 |
| JP | 5-049689 | 3/1993 |
| JP | 2002-315821 | 10/2002 |
| JP | 2004-089361 | 3/2004 |
| WO | 98/52623 | 11/1998 |

OTHER PUBLICATIONS http://www.merriam-webster.com/dictionary/constitutional, accessed Jan. 11, 2012.*
http://www.merriam-webster.com/dictionary/constituent, accessed Jan. 11, 2012.*

(Continued)

*Primary Examiner* — Paul Dickinson
(74) *Attorney, Agent, or Firm* — Greenblum & Bernstein, P.L.C.

(57) ABSTRACT

It is an object of the present invention to provide a polymer material, the histocompatibility of which has been improved by irradiation of ion beam, which prevents an aneurysm having a risk of rupture from actually rupturing. The present invention provides a material for treating aneurysms, which is composed of a polymer material containing carbon as a constitutional element, and which is produced by modifying at least a portion of the surface thereof by ion bombardment.

8 Claims, 7 Drawing Sheets

OTHER PUBLICATIONS

Sadasivan et al, Use of Experimental Aneurysms to Evaluate Wrapping Materials, Surg Neurol, 1990, 34, 3-7.*
Y. Suzuki et al., Journal of Surface Science Society of Japan, 1999, vol. 20, No. 9, pp. 634-639, with an English language abstract.
Y. Ono et al.; 21 Seiki Rengo Symposium Ronbunshu, Nov. 16, 2003, vol. 2, pp. 167-168.
Y. Murayama et al.; American Journal of Neuroradiology, 1999, vol. 20, pp. 1986-1991.
Y. Murayama et al.; American Journal of Neuroradiology, 1999, vol. 20, pp. 1992-1999.
Y. Suzuki et al.; Ionics, 1999, vol. 25, Sample 1, No. 284, pp. 47-54.
Y. Suzuki et al.; Ionics, vol. 27, No. 7, pp. 3-11, 2001.
Y. Murayama et al.; Neurosurgery, 1997, vol. 40, No. 6, pp. 1233-1244.
Y. Suzuki et al.; Nuclear Instruments and Methods in Physics Research, 1992, B65, pp. 142-147.
Y. Murayama et al.; Nuclear Instruments and Methods in Physics Research, 1997, B 127/128, pp. 1015-1018.
Y. Suzuki et al.; Polymers, 1992, vol. 41, No. 5, pp. 338-341.
International Search Report for PCT/JP2004/012138, mailed Nov. 9, 2004.
International Preliminary Report on Patentability for PCT/JP2004/012138, mailed May 26, 2006.
Taylor S. R. et al., "Effect of Surface Texture on the Soft Tissue Response to Polymer Implants" Journal of Biomedical Materials Research, vol. 17, No. 2, pp. 205-228, 1983.
Lee J.-S. et al., "Selective Adhesion and Proliferation of Cells on Ion-Implanted Polymer Domains" Biomaterials, vol. 14, No. 12, pp. 958-960, 1993.
Yotoriyama T. et al, "Ion-Beam Irradiated ePTFE for the Therapy of Intracranial Aneurysms" Abstract No. XP00 2537929, Database Medline, NLM15287485, 2004.
Suzuki et al., "Fibrin Glue and Tissue Adhesion to Ion Implanted ePTFE for the Application of Duramater" Polymer Preprints, Japan, vol. 52, No. 5, p. 1152, IIIPd186, May 8, 2003.
Suzuki et al., "Ion Beam Modification of ePTFE for the Application of Duramater" Polymer Preprints, Japan, vol. 50, No. 5, p. 1031, IIIPb148, 2001.
Pelissou-Guyotat et al., "The use of Teflon as wrapping material in aneurysm" *Neurological Research* vol. 16, No. 3, pp. 224-227, 1994.
Pelissou-Guyotat et al., "Wrapping and pledgets of Teflon in aneurysmal surgery: Technical Note" *Neurochirurgie*, vol. 39, No. 3, pp. 166-170, 1993.
"Application of wrapping technique in the surgically treated 689 cerebral aneurysms" Tohoku Nokekkanshogai Konnwakai Gakujutsushukai Kirokushu, vol. 19, pp. 23-32, 1997.
Noguchi et al., "Two Cases of Graft Replacement Combined with Wrapping Procedure for Thoracoabdominal Aortic Aneurysm" *Jpn. J. Cardiovasc. Surg.* vol. 25, No. 3, pp. 203-206, 1996.
Japanese Official Action issued in connection with Japanese Application 2003-207850, dated Feb. 16, 2010.
Supplementary European Search Report for EP 04 77 2099, 2011.

* cited by examiner (a)  (b)

(a)  (b)

(a)      (b)

(a)      (b)

MATERIAL FOR ANEURYSM CURING

CROSS-REFERENCE TO RELATED APPLICATIONS

This application is a Divisional of application Ser. No. 10/568,694, which is a National Stage of International Application No. PCT/JP2004/012138, filed Aug. 18, 2004. This application also claims priority of Japanese Application No. 2003-207850, filed Aug. 19, 2003. The entire disclosures of application Ser. No. 10/568,694 and PCT/JP04/12138 are considered as being part of this application, and the entire disclosure of each application is expressly incorporated by reference herein in their entirety.

DESCRIPTION

1. Technical Field

The present invention relates to a material for treating aneurysms, which can be used to treat aneurysms, and a production method thereof.

2. Background Art

Every year, subarachnoid hemorrhages caused by ruptured cerebral aneurysms occur to approximately 12 out of 100,000 people. More specifically, this malady occurs to approximately 15,000 people among a total population of 126,000,000 in Japan. Approximately 50% of such patients with subarachnoid hemorrhages die due to the first subarachnoid hemorrhage. Also, if a particular treatment is not given, 25% to 30% of such patients die due to rebleeding.

As a therapeutic method for treating aneurysms, the clipping of an aneurysm neck portion by craniotomy (FIG. 1a), or a method of forming a thrombus in an aneurysm portion by an intravascular treatment using a detachable coil (FIG. 1b), is adopted. Such methods are effective for a dome-shaped aneurysm, but in the treatment for a cerebral aneurysm having a risk of rupture called "wide neck aneurysm", the clipping can not be carried out, and also the treatment using a coil can not be applied because the coil is moved to a peripheral portion due to the flowing of bloodstream. In order to prevent such a wide neck type aneurysm from rupture, the affected area is wrapped with ePTFE fiber, an ePTFE sheet or silk fiber, and thereafter a living tissue adhesive called a fibrin glue is used. However, these materials are extremely poor in terms of affinity with a vascular wall and the adhesiveness of a fibrin glue. Thus, the materials often become detached, and it becomes impossible to prevent such rupture by strong wrapping in the actual situation. Accordingly, clinicians have desired a material for quickly and strongly wrapping such a wide neck type cerebral aneurysm, which is capable of preventing the rupture thereof.

Moreover, it has been proposed that a polymer material modified by ion bombardment be used for various types of biomaterials. For example, a cell-adhesive material, which is composed of a polymer material containing carbon as a constitutional element and which is produced by modifying at least a portion of the surface thereof by ion bombardment (Japanese Patent Application Laid-Open (Kokai) No. 5-49689), and a material for adhering to bone and/or fascia, which is composed of a polymer material containing carbon as a constitutional element and which is produced by modifying at least a portion of the surface thereof by ion bombardment (Japanese Patent Application Laid-Open (Kokai) No. 2002-315821), have been reported. In addition to the aforementioned examples, further examples of surface modification by ion bombardment are described in, for example, Endothelial Cell Adhesion to Ion Implanted Polymers, Y. Suzuki, M. Kusakabe, J.-S. Lee, M. Kaibara, M. Iwaki, and H. Sasabe, Nucl. Instr. and Meth., B65, (1992) pp. 142-147; Application of Ion Beam to Polymer Materials and Application to Artificial Dura Mater, Y. Suzuki, Y. Murakami, A. Nakao, M. Iwaki, M. Kaihabara, and M. Kamio, Ionics-Science and Technology of Ions, Vol: 25, No. 284 (1999) pp. 47-54; Surface Modification of Polymer by Ion Beam Application, Y. Suzuki, M. Kusakabe, and M. Iwaki, Polymers, Vol. 41, No. 5,338 (1992); Application of Ion Beam-Irradiated ePTFE to Artificial Dura Mater, Y. Suzuki, M. Iwaki, M. Kaibara, S. Tani, G. Ohashi, and M. Kamio, Ionics-Science and Technology of Ions, Vol: 27, No. 7 (2001) pp. 3-11; A New Surface Modification Technique of Platinum Coils by Ion Implantation and Protein Coating, Use in Intravascular Treatment of Brain Aneurysms, Y. Murayama, Y. Suzuki, F. Vinuela, T. F. Massoud, H. M. Do, G. Guglielmi, M. Iwaki, M. Kamio, and T. Abe, Nucl. Instr. and. Meth. in Phys. Res. B127/128 (1997) pp. 1015-1018; Ion Implantation and Protein Coating of Detachable Coils for Endovascular Treatment of Cerebral Aneurysmas: Concepts and Preliminary Results in Swine Models, Y. Murayama, F. Vinuela, Y. Suzuki, H. M. Do, T. F. Massoud, G. Guglielmi, D. Ji, M. Iwaki, M. Kusakabe, M. Kamio, and T. Abe, Neurosurgery, Vol. 40, No. 6 (1997) pp. 1233-1244; Development of a Biologically Active Guglielmi Detachable Coil for the Treatment of Cerebral Aneurysms, Part I: In Vitro Study, Y. Murayama, Y. Suzuki, F. Vinuela, M. Kaibara, K. Kurotobi, M. Iwaki, and T. Abe, AJNR Am J Neuroradiol 20:1986-1991 (1999); and Development of a Biologically Active Guglielmi Detachable Coil for the Treatment of Cerebral Aneurysms, Part II: An Experimental Study in a Swine Aneurysm Model, Y. Murayama, F. Vinuela, Y. Suzuki, Y. Akiba, A. Ulihoa, G. Duckwiler, Y. Gobin, H. Vinters, M. Iwaki, and T. Abe., AJNR Am J Neuroradiol 20: 1992-1999 (1999), and the like.

DISCLOSURE OF THE INVENTION

It is an object of the present invention to provide a polymer material, the histocompatibility of which has been improved by irradiation of ion beam, which prevents an aneurysm having a risk of rupture from actually rupturing.

Ion beam-irradiated ePTFE has cellular adhesiveness. When this material is used as a wrapping material for preventing the rupture of an aneurysm, it exhibits affinity with the outer wall of the blood vessel and has a rupture-preventing effect. In addition, when the rupture of an aneurysm occurs in the wrapping, the above material has a property of preventing the leakage of blood in the brain, because of its strong fixing ability. Moreover, since the above material has cellular adhesiveness, the self-repairing ability of the vascular wall is also improved. The preset invention has been completed based on these findings.

That is to say, the present invention provides a material for treating aneurysms, which is composed of a polymer material containing carbon as a constitutional element, and which is produced by modifying at least a portion of the surface thereof by ion bombardment.

Preferably, the polymer material containing carbon as a constitutional element is expanded polytetrafluoroethylene (ePTFE), polylactic acid, silicone, or silk.

Preferably, modification by ion bombardment is carried out by ion implantation using an ion beam with an acceleration energy that is between 1 keV and 2 MeV.

Preferably, modification by ion bombardment is carried out by ion implantation within a dose volume $\phi$ such that $1\times10^{12} \leq \phi < 1\times10^{17}$ ions/cm$^2$.

In another aspect, the present invention provides a method for producing a material for treating aneurysms, which is characterized in that ions are implanted into at least a portion of the surface of a polymer material containing carbon as a constitutional element, within a dose volume $\phi$ such that $1\times10^{12} \leq \phi < 1\times10^{17}$ ions/cm$^2$.

Preferably, the polymer material containing carbon as a constitutional element is expanded polytetrafluoroethylene (ePTFE), polylactic acid, silicone, or silk.

In another aspect, the present invention provides the use of a polymer material containing carbon as a constitutional material, at least a portion of the surface of which has been modified by ion bombardment, for the production of a material for treating aneurysms.

In a further aspect, the present invention provides a method for treating aneurysms, which comprises wrapping the aneurysm of a patient using a polymer material containing carbon as a constitutional material, at least a portion of the surface of which has been modified by ion bombardment.

BRIEF DESCRIPTION OF THE DRAWINGS

FIG. 1a shows the clipping of an aneurysm neck portion; FIG. 1b shows a therapeutic method involving the formation of a thrombus; and FIG. 1c shows wrapping (whereby the periphery of an aneurysm is wrapped with ePTFE).

BEST MODE FOR CARRYING OUT THE INVENTION

Figure 1:
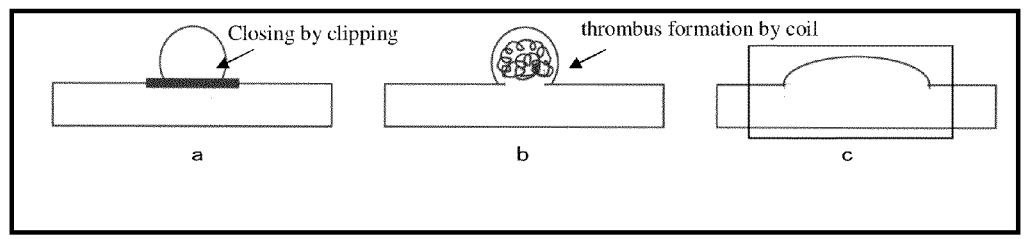
FIG. 1 shows the summary of a method for treating aneurysms.

The embodiments of the present invention will be described in detail below.

As stated above, as a therapeutic method of a wide neck type cerebral aneurysm, only a method comprising wrapping the entire aneurysm with a polymer material and then adhering it with a blood-derived adhesive called a fibrin glue, so as to prevent the rupture of the aneurysm, has been applied. At present, a material such as ePTFE or silk has been used. However, such a material has poor cellular adhesiveness, and has no affinity with the outer wall of the blood vessel. In addition, the fixing ability of the fibrin glue is considerably weak in the actual situation.

An ion beam-irradiated polymer material such as ePTFE has cellular adhesiveness, and also has affinity with the wrapped outer wall of the blood vessel. Even when the rupture of an aneurysm has occurred in the inside of the wrapping, since the above material has strong fixing ability, it is able to prevent the blood from leaking into the brain. Moreover, since the above material has cellular adhesiveness, the self-repairing ability of the vascular wall is also improved. Furthermore, as a result of in vitro experiments and animal experiments, it became clear that the adhesiveness of a fibrin glue is significantly improved by irradiation of ion beam. The use of this material enables a more complete treatment of an unruptured aneurysm. That is to say, the present invention relates to a material for treating aneurysms, which is formed by irradiation of ion beam to a polymer material (for example, expanded polytetrafluoroethylene, polylactic acid, silicone, silk, etc.), so as to impart cellular adhesiveness thereto.

The type of a polymer material containing carbon as a constitutional element used in the present invention is not particularly limited, as long as it is a material having biocompatibility and good handlability, and any given material can be used. Examples of a polymer material preferably used in the present invention may include expanded polytetrafluoroethylene (ePTFE), polylactic acid, silicone, and silk. Of these, expanded polytetrafluoroethylene (ePTFE) is particularly preferable.

At least a portion of the surface of a polymer material used for the material for treating aneurysms of the present invention is modified by ion bombardment. Examples of the type of ion species implanted may include H$^+$, He$^+$, C$^+$, N$^+$, Ne$^+$, Na$^+$, N$^+$, O$^+$, Ar$^+$, and Kr$^+$. However, the type of ion species is not particularly limited to the above examples, unless it elutes to inhibit the growth of cells.

A dose volume $\phi$ is preferably $1\times10^{12} \leq \phi < 1\times10^{17}$ ions/cm$^2$. If such a dose volume is lower than $1\times10^{12}$ ions/cm$^2$, an effect of significantly improving cellular adhesiveness decreases. In contrast, if it is higher than $1\times10^{17}$ ions/cm$^2$, the polymer material is easily disrupted. Thus, both cases are not favorable. Such a dose volume $\phi$ is more preferably $1\times10^{13} \leq \phi < 1\times10^{16}$ ions/cm$^2$.

With regard to ion acceleration energy, it is considered that an energy transmission mechanism differs depending on the longitudinal level of the energy. Such an acceleration energy is practically between 1 keV and 5 MeV. For example, it is between 1 keV and 3 MeV. The lower limit of the acceleration energy can be set at 1 keV, 2 keV, 3 keV, 5 keV, 10 keV, 20 keV, 30 keV, 50 keV, or 100 keV, for example. On the other hand, the upper limit of the acceleration energy can be set at 5 MeV, 3 MeV, 2 MeV, or 1 MeV. Thus, the ion acceleration energy can be within the range of any given combination of the aforementioned lower and upper limits.

A beam current density is preferably set at approximately 0.5 μA/cm$^2$ or less. This is because if such beam current density is excessive, the temperature of a polymer material as a target extremely increases, and thus the polymer material itself deteriorates and there is a risk that cellular adhesiveness decreases.

An example of a means for giving ion bombardment in the present invention is ion implantation. In the case of ion implantation, the reaction itself is limited to an interaction between ion beam and a material to which ions are to be implanted (target material). In addition, by selecting an ion incident energy, ions can be embedded into any given depth from the surface. Thus, ion implantation has extremely good controllability. This is a characteristic, which a plasma treatment does not have. The implanted ions have a mechanism of exhibiting an electron stopping power against ions having a relatively light mass at the initial stage of diffusion, and exhibiting a nuclear stopping ability against ions having a relatively heavy mass from the beginning. Anyway, the implanted ions bring on the heating of the polymer material due to lattice vibration (thermal non-equilibrium state), and cause fusion, amorphization, or the like.

The present invention will be more specifically described in the following examples. However, these examples are not intended to limit the scope of the present invention.

EXAMPLE 1

Wrapping Material

Figure 2:
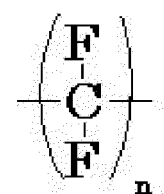
FIG. 2 shows the structural formula of ePTFE.

In the present example, Gore-Tex ePTFE patch II/pericardial sheet (PSM-01200) with a thickness of 0.1 mm (manufactured by Gore-Tex) was used. FIG. 2 shows the structural formula of ePTFE. An aseptically packed PSM-01200 was opened. After an ion beam had been irradiated thereto, it was sterilized with ethylene oxide gas (EOG) for animal experiments.

EXAMPLE 2

Ion Beam-irradiation

An ion beam-irradiated sample was produced at an acceleration voltage of 150 keV in an amount irradiated of $5 \times 10^{14}$ $Ar^+$ ions/cm$^2$ and $1 \times 10^{14}$ $Kr^+$ ions/cm$^2$, using an ion implanter, RIKEN 200 kV Low Current Implanter. Irradiation was carried out at an ion beam current of 0.05 μA/cm$^2$.

EXAMPLE 3

Physicochemical Properties (1) Observation of Surface Form with Field Emission Scanning Electron Microscope (FE-SEM, Manufactured by Jeol, JSM6330F)

Figure 3:
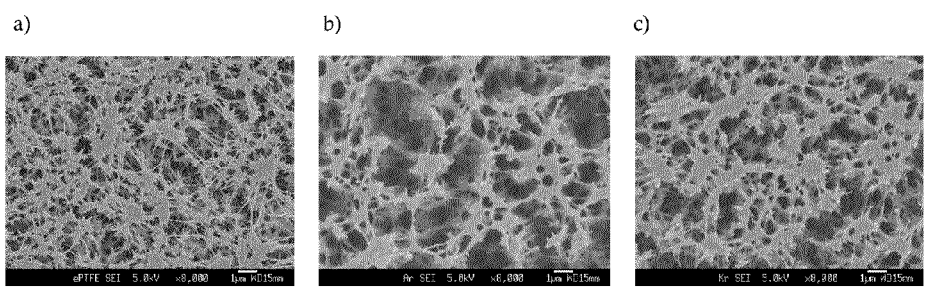
FIG. 3 shows SEM images (×8,000) of (a) unirradiated ePTFE; (b) $5\times10^{14}$ Ar$^+$-irradiated sample; and (c) $1\times10^{14}$ Kr$^+$-irradiated sample.

SEM images (×8,000) of (a) unirradiated ePTFE, (b) $5 \times 10^{14}$ $Ar^+$ ions/cm$^2$ irradiated sample, and (c) $1 \times 10^{14}$ $Kr^+$ ions/cm$^2$ irradiated sample, are shown in FIG. 3.

When an irradiated sample is compared with an unirradiated sample, the unirradiated sample has a higher density than that of the irradiated sample, and also has larger quantities of filamentous portions between nodes than in the case of the irradiated sample. This is because such bonds are cleaved by irradiation of ions. When an $Ar^+$-irradiated sample is compared with a $Kr^+$-irradiated sample, the $Ar^+$-irradiated sample has greater damage.

(2) Measurement by Attenuated Total Reflectance Fourier Transform Infrared Spectrophotometry (FT-IR-ATR Method)

Functional groups generated by ion implantation and bond cleavage were measured by the attenuated total reflectance Fourier transform infrared spectrophotometry (Nexsus 470 manufactured by Nicolet). The measurement was carried out under conditions of an internal element of Ge 45°, a resolution of cm$^{-1}$, and an accumulation number of 200.

Figure 4:
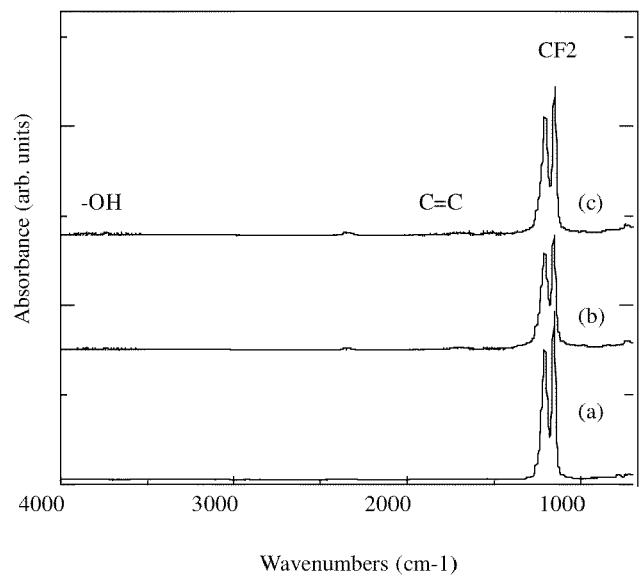
FIG. 4 shows the FT-IR-ATR spectra of (a) unirradiated ePTFE; (b) $5\times10^{14}$ Ar$^+$-irradiated sample; and (c) $1\times10^{14}$ Kr$^+$-irradiated sample.

FIG. 4 shows FT-IR-ATR spectra. It was observed that the double bonds of —OH groups and carbon atoms were increased by ion implantation in the order of control, Kr, and Ar, and that $CF_2$ was decreased in the order of control, Kr, and Ar.

Based on the relationship between the amount of functional groups generated and the amount of $CF_2$ decomposed, $CF_2$ is decomposed by irradiation of an ion beam, and as a result, carbon-carbon double bonds are formed. Irradiation of an $Ar^+$ ion beam having a larger amount of decomposition causes a larger amount of functional groups generated.

(3) Measurement by Raman Microspectroscopy

Figure 5:
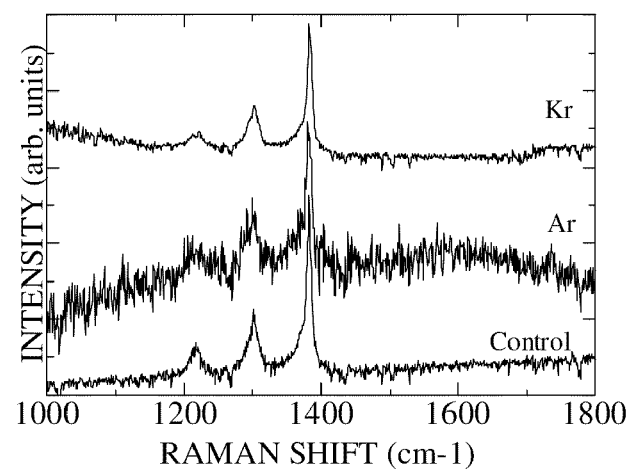
FIG. 5 shows the Raman spectrum of ePTFE sample.

The samples were analyzed by the Raman microspectroscopy (LabRam manufactured by Joban Yvon). Measurement conditions consisted of a He—Ne laser of 632.817 nm and an accumulation number of 5-times/3 sec. FIG. 5 shows a Raman spectrum.

It was observed that $CF_2$ was decreased in the order of control, Kr, and Ar, and that carbon-carbon double bonds were increased in the order of control, Kr, and Ar.

(4) Experiment Regarding Cellular Adhesiveness

Figure 6:
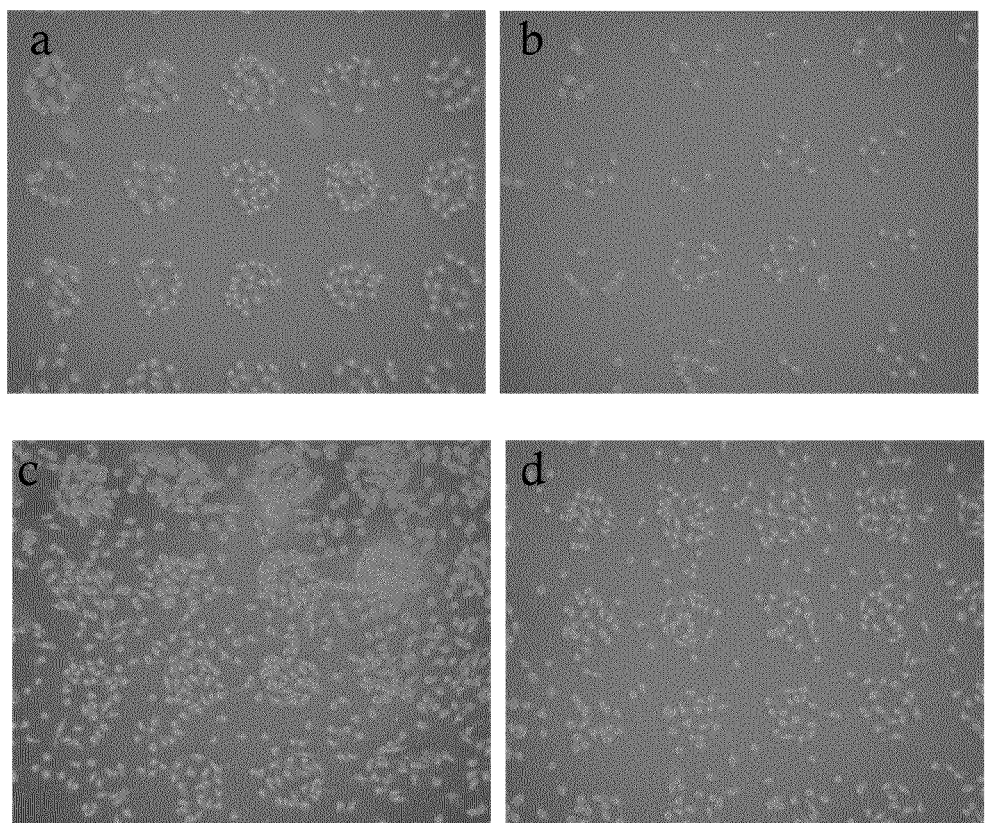
FIG. 6 shows images of cultured cells observed with a phase contract microscope:
(a) Ar$^+$, $5\times10^{14}$, on the first day;
(b) Kr$^+$, $1\times10^{14}$, on the first day;
(c) Ar$^+$, $5\times10^{14}$, on the second day; and
(d) Kr$^+$, $1\times10^{14}$, on the second day.

A sample, which had been patterned to a round shape of approximately 100 microns by irradiation, was sterilized with ultraviolet ray. Thereafter, the resultant sample was placed in a Petri dish with a diameter of 60 mm, and 5 ml of a suspension of L929 ($2.5 \times 10^4$ cells/ml) was then added dropwise thereto. The obtained mixture was cultured for several days in an incubator at 37° C. in the presence of 5% $CO_2$. After completion of the culture, the obtained culture product was washed with a phosphate buffer (PBS(-)) twice, and the resultant product was then fixed with 2% glutaraldehyde in a refrigerator for 1 hour. Thereafter, the obtained product was dehydrated in 50%, 70%, 90%, and 100% ethanol ascending series. ePTFE, which became transparent as a result of immersion in 100% ethanol, was observed with a phase contrast microscope at a magnification of 100-fold. Images of cultured cells observed with a phase contract microscope are shown in FIG. 6.

L929 fibroblasts hardly adhere to an unirradiated ePTFE portion, but these cells selectively adhere to an ion beam irradiated portion. In addition, at an initial stage, the cells more significantly adhere to an $Ar^+$ ion beam-irradiated portion than to a $Kr^+$ ion beam irradiated portion.

EXAMPLE 4

Animal Experiment

Figure 7:
FIG. 7 shows the state of the sample of the present invention after a rabbit carotid artery has been wrapped with the above sample.

For in vivo (in living bodies) evaluation, 13 Japanese white rabbits (with a body weight between 3 and 4.5 kg) were subjected to the experiment. Two types of samples were produced by irradiating $5 \times 10^{14}$ $Ar^{++}$ or $1 \times 10^{14}$ $Kr^+$ at an acceleration energy of 150 keV to the entire surface of Gore-Tex ePTFE patch II/pericardial sheet (PSM-01200) with a thickness of 0.1 mm manufactured by Gore-Tex. The carotid artery of each of the above rabbits was wrapped with such two types of samples. The upstream side of the blood vessel was just wrapped. In order to observe self-repairing ability, the downstream side thereof was wrapped such that the ion-irradiated surface was allowed to come into contact with the blood vessel, after the outer membrane had been eliminated. Thereafter, the downstream side was fixed with a plasma derivative living tissue adhesive Bolheal (manufactured by Kaketsuken, the Chemo-Sero-Therapeutic Research Institute), and it was then clipped. The experiment was carried out for an acute case (1 week) and chronic cases (1 month, 3 months). FIG. 7 shows the state of the sample after a rabbit carotid artery has been wrapped with the above sample.

Figure 8:
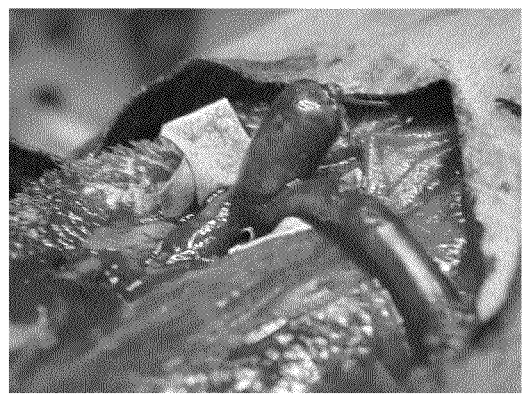
FIG. 8 shows an aneurysm model produced in the carotid artery of a beagle dog.
Figure 9:
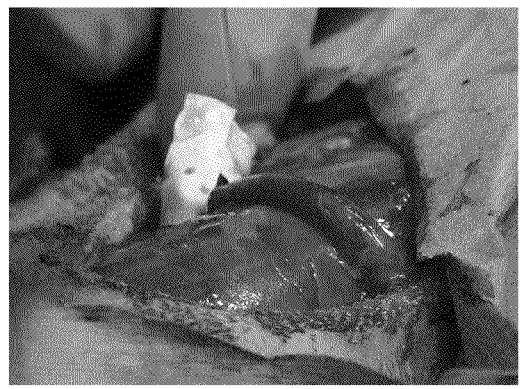
FIG. 9 shows the state of a wrapped aneurysm of a beagle dog.

Moreover, aneurysm models were produced from 5 mature beagle dogs (with a body weight of 10 kg). Thereafter, an experiment was carried out, wherein the sample was attached to the periphery of the aneurysm area only with the plasma derivative living tissue adhesive Bolheal. FIG. 8 shows an aneurysm model. FIG. 9 shows the state of a wrapped aneurysm of a beagle dog.

The carotid artery of a rabbit, which had been wrapped by the aforementioned method, was excised, and it was then fixed with formalin. Thereafter, it was stained with hematoxylin and eosin (HE) and was then observed with a phase contrast microscope. Thereafter, the material used for wrapping the rabbit carotid artery was subjected to a histological test.

Figure 10:
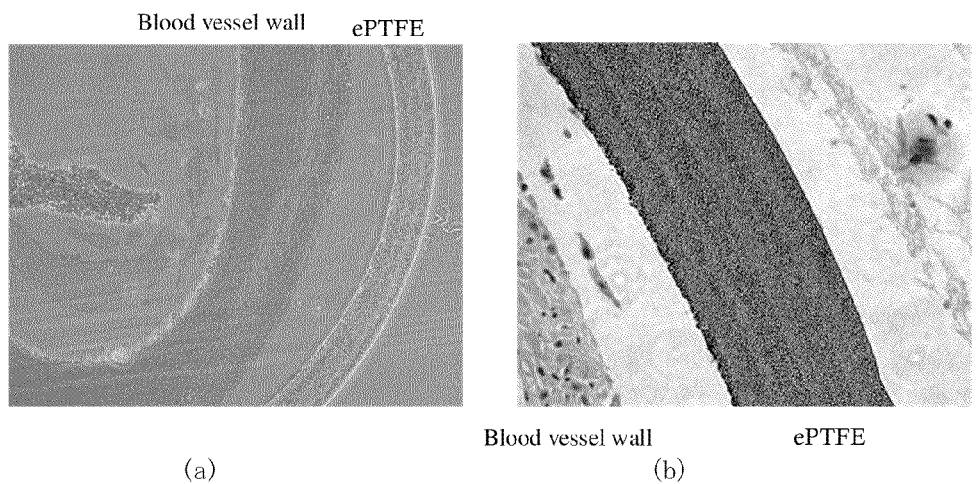
FIG. 10 shows a histological photograph of unirradiated ePTFE (3 months) used to wrap a rabbit carotid artery. (a) indicates 100-fold, and (b) indicates 400-fold.

FIG. 10 shows a histological photograph of the sample used to wrap unirradiated ePTFE. (a) was observed at a magnification of 100-fold, and (b) was observed at a magnification of 400-fold. The unirradiated sample did not adhere to the vascular wall.

Figure 11:
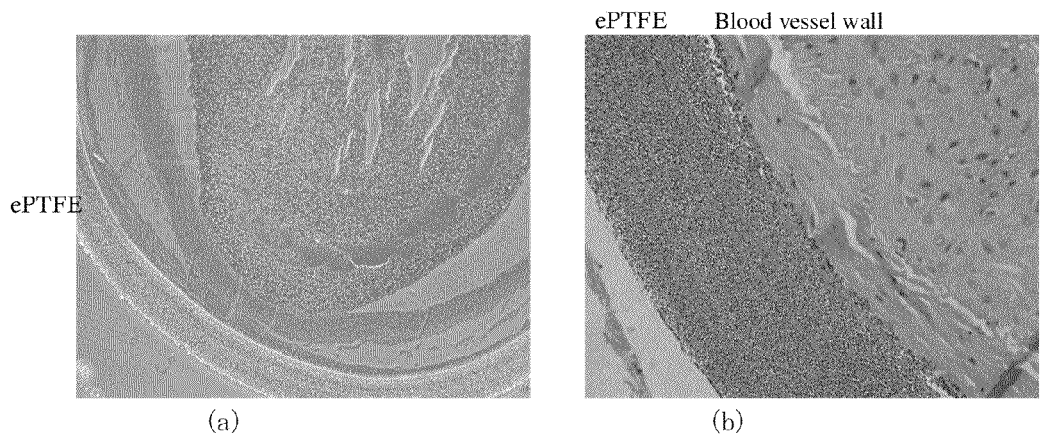
FIG. 11 shows a histological photograph of Ar$^+$-irradiated ePTFE (1 week) used to wrap a rabbit carotid artery. (a) indicates 100-fold, and (b) indicates 400-fold.

FIG. 11 shows a histological photograph of $5 \times 10^{14}$ Ar$^+$-irradiated material (1 week). The Ar$^+$-irradiated material showed a good adhesion to the vascular wall.

Figure 12:
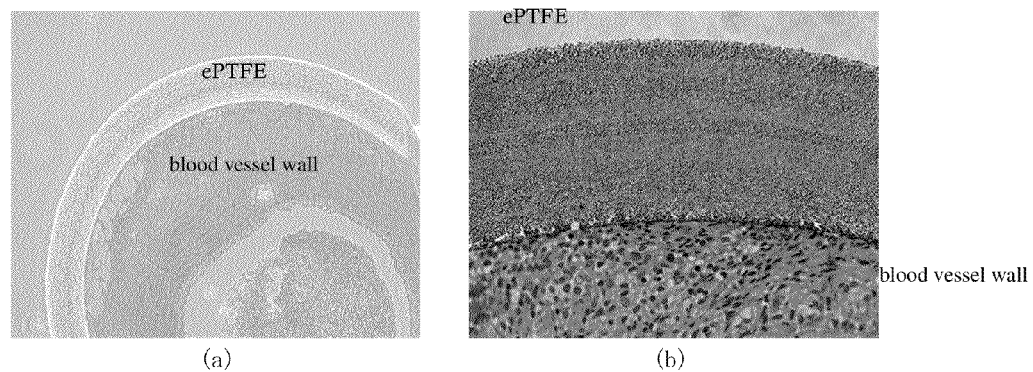
FIG. 12 shows a histological photograph of Kr$^+$-irradiated material (1 week) used to wrap a rabbit carotid artery. (a) indicates 100-fold, and (b) indicates 400-fold.

FIG. 12 shows a histological photograph of $1 \times 10^{14}$ Kr$^+$-irradiated material (1 week) used to wrap a rabbit carotid artery. As in the case of the Ar$^+$-irradiated sample, the Kr$^+$ irradiated surface showed good adhesion to the vascular wall.

Figure 13:
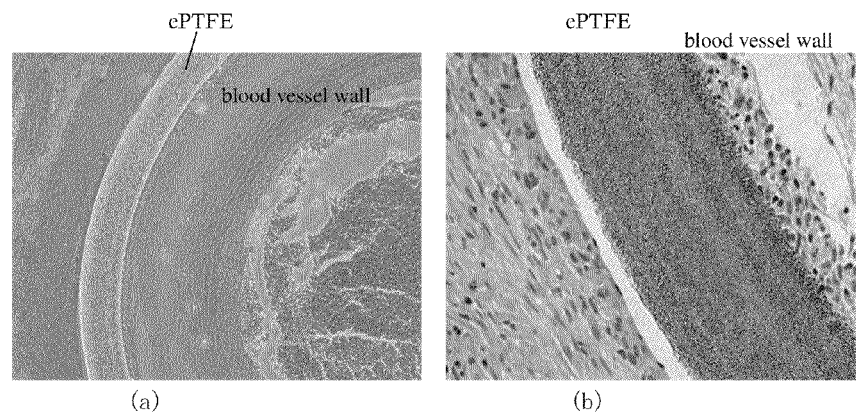
FIG. 13 shows a histological photograph of Ar$^+$-irradiated ePTFE (1 month) used to wrap a rabbit carotid artery. (a) indicates 100-fold, and (b) indicates 400-fold.

FIG. 13 shows a histological photograph of $5 \times 10^{14}$ Ar$^+$-irradiated material (1 month). It was observed that the vascular wall adhering to the irradiated surface had been repaired.

Figure 14:
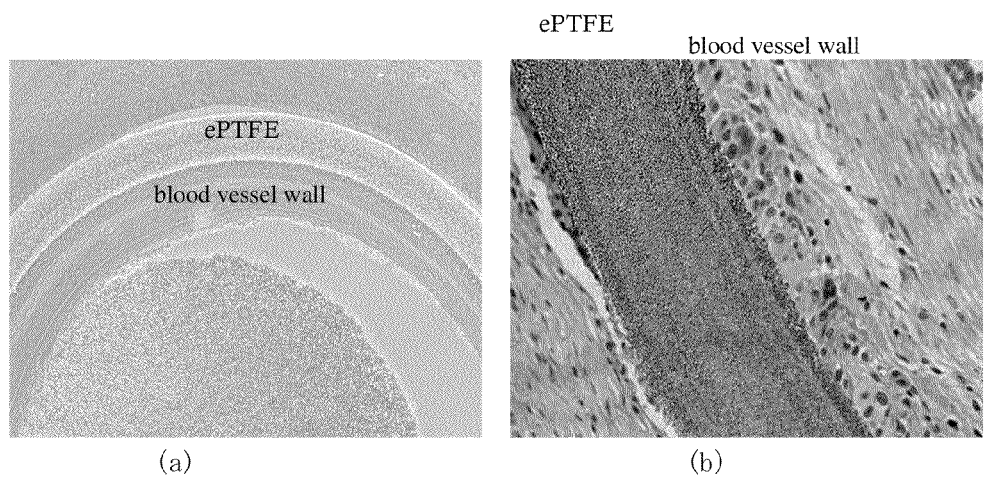
FIG. 14 shows a histological photograph of Kr$^+$-irradiated material (1 month) used to wrap a rabbit carotid artery. (a) indicates 100-fold, and (b) indicates 400-fold.

FIG. 14 shows a histological photograph of $1 \times 10^{14}$ Kr$^+$-irradiated material (1 month) used to wrap a rabbit carotid artery. As in the case of the Ar$^+$-irradiated sample, the Kr$^+$-irradiated surface showed a good adhesion to the vascular wall, and the repaired state was also good.

From the results shown in these histological photographs, it became clear that the unirradiated ePTFE portion does not have adhesiveness to the vascular wall, but that the ion beam-irradiated portion has such adhesiveness. When the affected area is wrapped with ion beam-irradiated ePTFE, self-repairing ability was observed in a portion, from which the outer membrane had been eliminated. From these results, it is found that, by wrapping the outer wall of an aneurysm having a risk of rupture with the present material, a sufficient effect of preventing the rupture can be achieved.

Industrial Applicability

The present invention provides a material having biocompatibility which is capable of treating aneurysms, and a production method thereof. The material for treating aneurysms of the present invention has both, adhesiveness to the vascular wall and self-repairing ability, and it can effectively treat aneurysms.

The invention claimed is:

1. A method for treating aneurysms, comprising wrapping the outer wall of an aneurysm of a patient with a polymer material comprising expanded polytetrafluoroethylene (ePTFE), polylactic acid, silicone, or silk, which polymer material is produced by modifying at least a portion of the surface thereof by particle bombardment.

2. The method according to claim 1, wherein modification by particle bombardment is carried out by ion implantation using an ion beam with an acceleration energy that is between 1 keV and 2 MeV.

3. The method according to claim 1, wherein modification by particle bombardment is carried out by ion implantation within a dose volume $\phi$ such that $1 \times 10^{12} \leq \phi \leq 1 \times 10_{17}$ ions/cm$^2$.

4. The method according to claim 1, wherein the polymer material comprises ePTFE.

5. The method according to claim 1, wherein the polymer material comprises polylactic acid.

6. The method according to claim 2, wherein modification by particle bombardment is carried out by ion implantation within a dose volume $\phi$ such that $1 \times 10^{12} \leq \phi \leq 1 \times 10_{17}$ ions/cm$^2$.

7. The method according to claim 1, wherein the polymer material comprises silicone.

8. The method according to claim 1, wherein the polymer material comprises silk.

* * * * *